United States Patent
Ein-Gal (10) Patent No.: US 7,298,821 B2
(45) Date of Patent: Nov. 20, 2007

(54) IMAGING AND TREATMENT SYSTEM

(76) Inventor: Moshe Ein-Gal, 30 Azar Street, Ramat Hasharon 47203 (IL)

( * ) Notice: Subject to any disclaimer, the term of this patent is extended or adjusted under 35 U.S.C. 154(b) by 134 days.

(21) Appl. No.: 11/298,826

(22) Filed: Dec. 12, 2005

(65) Prior Publication Data

US 2007/0133752 A1    Jun. 14, 2007

(51) Int. Cl.
  *A61B 6/08* (2006.01)
  *A61N 5/10* (2006.01)

(52) U.S. Cl. .......................... 378/68; 378/65; 378/205

(58) Field of Classification Search .................. None
  See application file for complete search history.

(56) References Cited

U.S. PATENT DOCUMENTS

| | | | | |
|---|---|---|---|---|
| 4,649,560 A | * | 3/1987 | Grady et al. | 378/196 |
| 5,189,687 A | * | 2/1993 | Bova et al. | 378/65 |
| 5,207,223 A | * | 5/1993 | Adler | 600/427 |
| 5,351,280 A | * | 9/1994 | Swerdloff et al. | 378/65 |
| 5,583,908 A | * | 12/1996 | Antich et al. | 378/65 |
| 6,031,888 A | * | 2/2000 | Ivan et al. | 378/20 |
| 6,385,288 B1 | * | 5/2002 | Kanematsu | 378/65 |
| 6,614,871 B1 | * | 9/2003 | Kobiki et al. | 378/20 |
| 6,888,919 B2 | * | 5/2005 | Graf | 378/65 |
| 6,914,959 B2 | * | 7/2005 | Bailey et al. | 378/65 |
| 7,014,361 B1 | * | 3/2006 | Ein-Gal | 378/197 |
| 7,130,372 B2 | * | 10/2006 | Kusch et al. | 378/65 |
| 7,200,202 B2 | * | 4/2007 | Kusch et al. | 378/65 |

* cited by examiner

*Primary Examiner*—Edward J. Glick
*Assistant Examiner*—Thomas R. Artman
(74) *Attorney, Agent, or Firm*—Dekel Patent Ltd.; David Klein (57) ABSTRACT

An imaging device including a rotator having a hollow bore for a patient to move therein and thereout, the rotator being rotatable about a longitudinal axis, at least one linkage arm extending outwards from the rotator, and imaging apparatus mounted on the at least one linkage arm, the imaging apparatus including an imaging source that emits an imaging beam to an imaging detector aligned therewith along an imaging direction, the at least one linkage arm capable of full axial rotation about an imaging isocenter along an entire length of the patient, the isocenter lying along a longitudinal axis, and wherein the imaging apparatus is operative to rotate and to capture images of the patient along the imaging direction as the patient is positioned at an angle in a range of about 0-90° inclusive with respect to the longitudinal axis.

8 Claims, 7 Drawing Sheets

IMAGING AND TREATMENT SYSTEM

FIELD OF THE INVENTION

The present invention relates generally to imaging and treatment systems, such as but not limited to, an x-ray or fluoroscope imaging system combined with a linear accelerator, wherein a spatial relationship is maintained between the imaging system and the treatment system such that beams from both systems intersect at a common isocenter.

BACKGROUND OF THE INVENTION

A CT (computerized tomography) scanner has a large hollow bore into which a patient is inserted longitudinally for imaging. The patient moves generally longitudinally with respect to the scanner (which is typically stationary), and the scanning may be done for a full revolution about the longitudinal axis. No rotation is available for other axes. If need be, the patient can be moved afterwards to a treatment area.

A typical prior art C-arm is a device with an imaging source (e.g., x-ray generator) mounted on one end of the C-arm and an image detector on the other end of the C-arm. The C-arm is a mobile device, and is therefore heavily used in treatment rooms. The construction does not typically allow full axial rotations but provides some limited rotations about a longitudinal axis through the patient (i.e., partial roll) and a vertical axis not through the patient (i.e., partial azimuth).

Imaging devices are also used to assist in target localization in conjunction with treatment equipment having its own rotating gantry, e.g., a linear accelerator (LINAC). However, the imaging device typically moves independently of the gantry of the treatment device. In other words, the coordinate system of the imaging device is separate and independent of the coordinate system of the treatment device. Since localization is required in the treatment device coordinate system, the respective coordinate systems of the imaging and the treatment devices have to be aligned or registered with respect to each other.

An isocentric treatment device, e.g., a linear accelerator, is operable to rotate a treatment head (e.g., a gantry arm with a radiation source disposed therein) having a treatment direction (e.g., the direction of a radiation beam) about a generally horizontal treatment axis (e.g., the longitudinal axis along a patient couch), wherein said treatment direction intersects with said treatment axis at an isocenter. Such an isocentric treatment device may be coupled to a couch operable to rotate (e.g., in azimuth) about a generally vertical couch axis intersecting said isocenter.

An imaging device having an imaging direction (that is, a direction along which an imaging beam is directed) may be added to such an isocentric treatment device for target localization. The imaging device rotates about a generally horizontal imaging axis intersecting with the isocenter. Usually, the treatment axis and the imaging axis coincide, e.g., the imaging device is mounted on the treatment head and rotates with it. However, the prior art has the disadvantage of the imaging axis not being parallel to the couch longitudinal direction for all couch angles.

SUMMARY OF THE INVENTION

The present invention seeks to provide a novel system for imaging and for coupling an imaging system to a treatment device, as is described more in detail hereinbelow.

The invention combines advantages of a CT scanner and a C-arm device. The system of the invention may incorporate a large hollow bore rotator allowing full axial rotations. The system is mobile and allows transversal rotation about a patient while maintaining a fixed mechanical relationship with the rotator to avoid collision. In a non-limiting embodiment of the present invention, the imaging system may be coupled to a rotating gantry, and a known geometrical relationship is maintained such that target localization by the imaging system (which may resemble a c-arm) is directly coupled to the gantry. A spatial relationship is maintained between the imaging system and the treatment system such that beams from both systems intersect at a common isocenter, as described in detail hereinbelow.

For example, in one non-limiting embodiment of the invention, the imaging system is coupled to an isocentric treatment device such that the imaging axis of the imaging system intersects the isocenter while staying parallel to the longitudinal direction of a patient support (couch) for all couch angles. The coupler that connects the imaging device to the treatment device maintains a fixed angle between the treatment direction and the imaging direction throughout a range of treatment, imaging and couch angles.

There is provided in accordance with an embodiment of the present invention an imaging device including a rotator having a hollow bore for a patient to move therein and thereout, the rotator being rotatable about a longitudinal axis, at least one linkage arm extending outwards from the rotator, and imaging apparatus mounted on the at least one linkage arm, the imaging apparatus including an imaging source that emits an imaging beam to an imaging detector aligned therewith along an imaging direction, the at least one linkage arm capable of full axial rotation about an imaging isocenter along an entire length of the patient, the isocenter lying along a longitudinal axis, and wherein the imaging apparatus is operative to rotate and to capture images of the patient along the imaging direction as the patient is positioned at an angle in a range of about 0-90° inclusive with respect to the longitudinal axis.

A patient support member may be provided which is movable to cause relative motion between the patient and the imaging isocenter. The rotator may be rotatingly mounted to a stationary ring fixed to a portable frame. Coupling arms may be pivotally attached to the linkage arms at pivots. The coupling arms may be rotatingly attachable to a treatment device, such as by means of an interface member formed with an aperture for a treatment beam to pass therethrough. The treatment device may be rotatable about a treatment isocenter lying on a rotation axis and may emit a treatment beam along a treatment direction, wherein the treatment isocenter is located at an intersection of the rotation axis and the treatment direction. The treatment isocenter generally coincides with the imaging isocenter at a common isocenter. The patient support member may be rotatable about an axis intersecting the common isocenter. The coupling arms may maintain a fixed angle between the treatment direction and the imaging direction for a range of treatment device angles and imaging angles.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
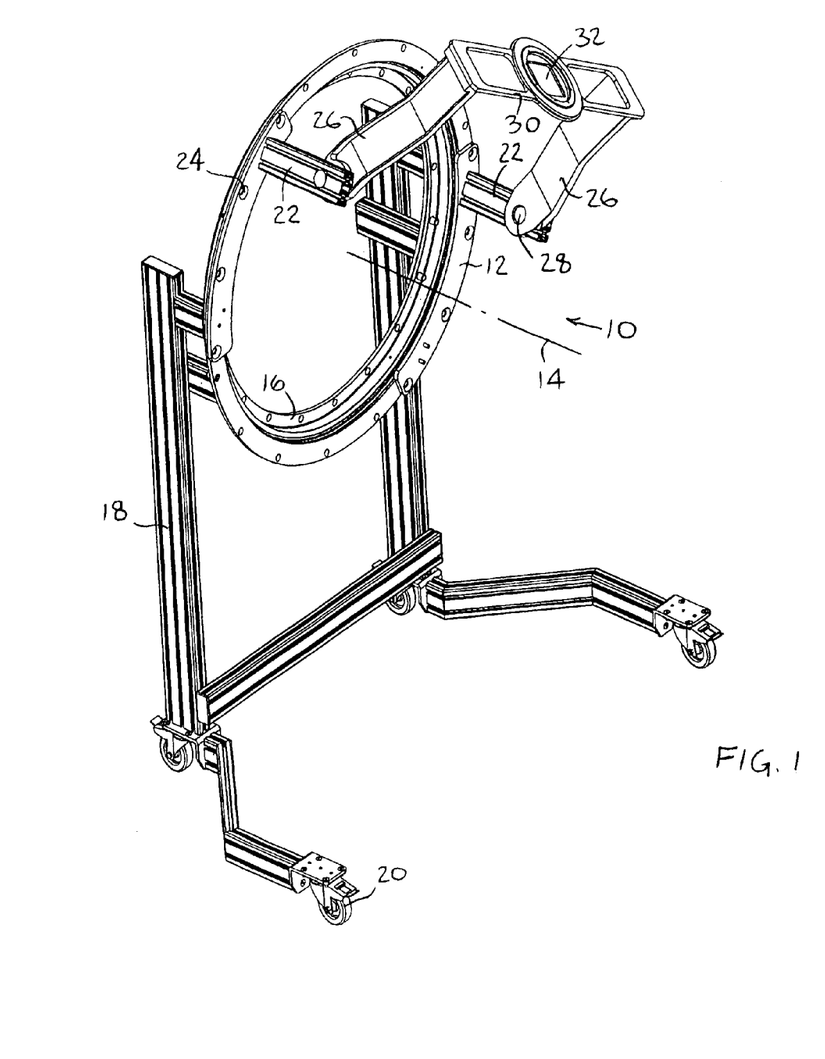
FIG. 1 is a simplified pictorial illustration of a coupler for an imaging system, constructed and operative in accordance with an embodiment of the present invention.

Reference is made to FIG. 1, which illustrates a coupler 10 for an imaging system, constructed and operative in accordance with an embodiment of the present invention.

The coupler 10 may include a rotator 12 having a hollow bore 50 for a patient to move therein and thereout. Although rotator 12 is shown as a ring, it does not necessarily have to be a ring, but rather any structure with hollow bore 50. Rotator 12 is rotatable about a longitudinal axis 14. For example, rotator 12 may be rotatingly mounted (e.g., by ball bearing races) to a stationary ring 16 that is fixed to a frame 18. Frame 18 may be portable, such as by being mounted on wheels or castors 20. One or more linkage arms 22 may extend from rotator 12. As seen in FIG. 1, linkage arms 22 may be attached to different mounting provisions 24 (e.g., mounting holes on rotator 12) spaced about axis 14. For example, linkage arms 22 may be mounted 180° part on rotator 12, or at any other angular separation. One or more coupling arms 26 may be pivotally attached to linkage arms 22 at pivots 28. Coupling arms 26 may be rotatingly mounted on a turret of a treatment device by means of an interface member 30, as shown and described further below with reference to FIG. 3. The interface member 30 may be a bar or similar structure that connects coupling arms 26 together. The interface member 30 may have an aperture 32 formed therein for a treatment beam to pass therethrough.

Figure 2:
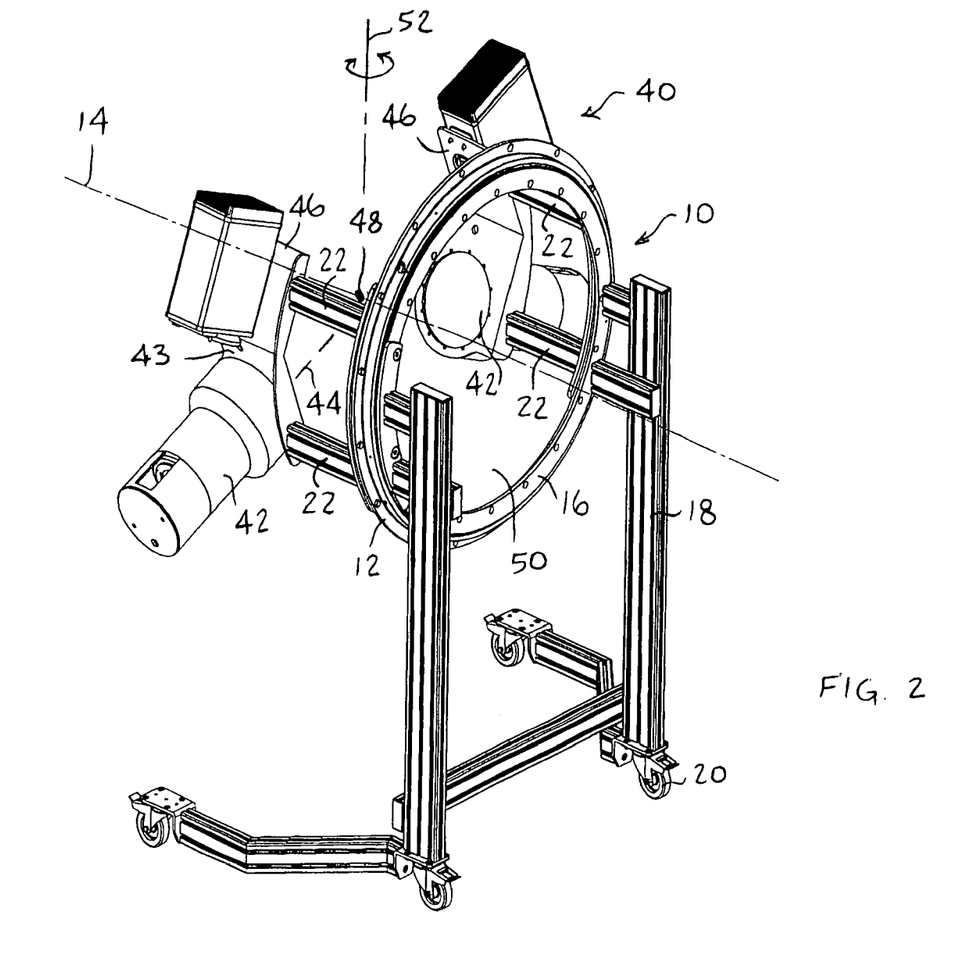
FIG. 2 is a simplified pictorial illustration of the coupler of FIG. 1 with imaging apparatus mounted thereon, in accordance with an embodiment of the present invention.

Reference is made to FIG. 2, which illustrates the coupler 10 with imaging apparatus 40 mounted thereon, in accordance with an embodiment of the present invention. The imaging systems 40 may include an imaging source 42 (e.g., x-ray source) that emits an imaging beam 44 (e.g., x-ray beam) along an imaging direction to an imaging detector 46 (e.g., x-ray detector) aligned therewith. The imaging apparatus 40 may include image processing equipment (not shown) for processing images captured by the imaging detector 46. The imaging source 42 and the imaging detector 46 may be mounted on linkage arms 22, or alternatively, on other arms cantilevered from rotator 12. Imaging beam 44 intersects longitudinal axis 14 at an imaging isocenter 48. Although the invention may be carried out with any number of imaging sources 42 and imaging detectors 46, in the non-limiting illustrated embodiment of FIG. 2, a pair of imaging sources 42 and imaging detectors 46 is mounted on pads 43 at the end of arms 22.

Rotator 12 defines a hollow bore 50 for a patient to move therein and thereout. It is noted that in a prior art C-arm, a patient cannot be moved longitudinally past the pivot point of the C-arm. In contrast, in the present invention, the patient may be moved unrestricted in and out of the hollow bore 50 along axis 14, and at the same time, the linkage arms 22 are capable of full axial rotation about the imaging isocenter 48 along the entire length of the patient. Moreover, in the present invention, the patient may be at least partially rotated about another axis 52, transverse to the longitudinal axis 14 (such as a vertical (azimuth) axis 52 that passes through isocenter 48), and imaging apparatus 40 may still capture images of the patient as he/she is rotated about axis 52. In general, the imaging apparatus 40 may rotate and may capture images of the patient along the imaging direction of imaging beam 44 as the patient is positioned at an angle in a range of about 0-90° inclusive with respect to the longitudinal axis 14. The patient may be moved out of hollow bore 50 and positioned perpendicularly to the longitudinal axis 14, wherein the coupler 10 and imaging apparatus 40 may be operated similarly to a C-arm.

Figure 3:
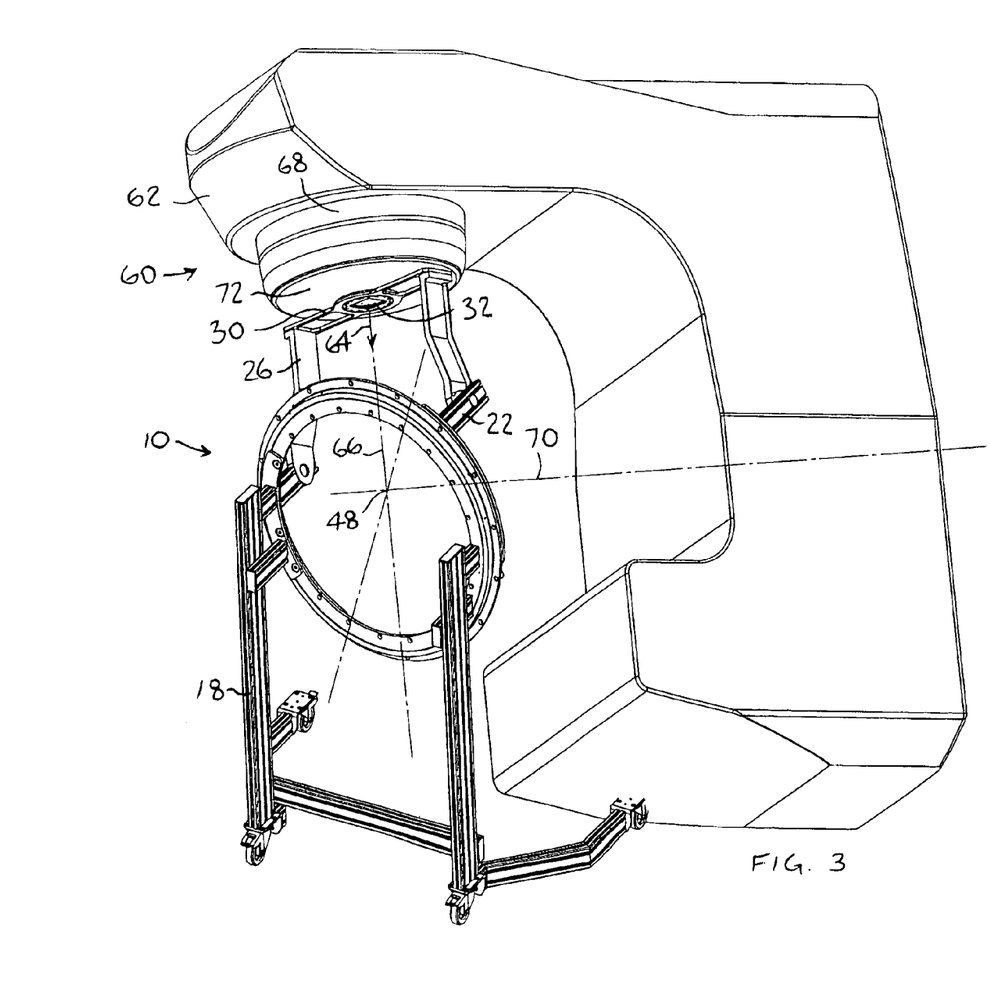
FIG. 3 is a simplified pictorial illustration of an imaging and treatment system, wherein the coupler and imaging system of FIG. 1 is attached to a treatment system, constructed and operative in accordance with an embodiment of the present invention.
Figure 4:
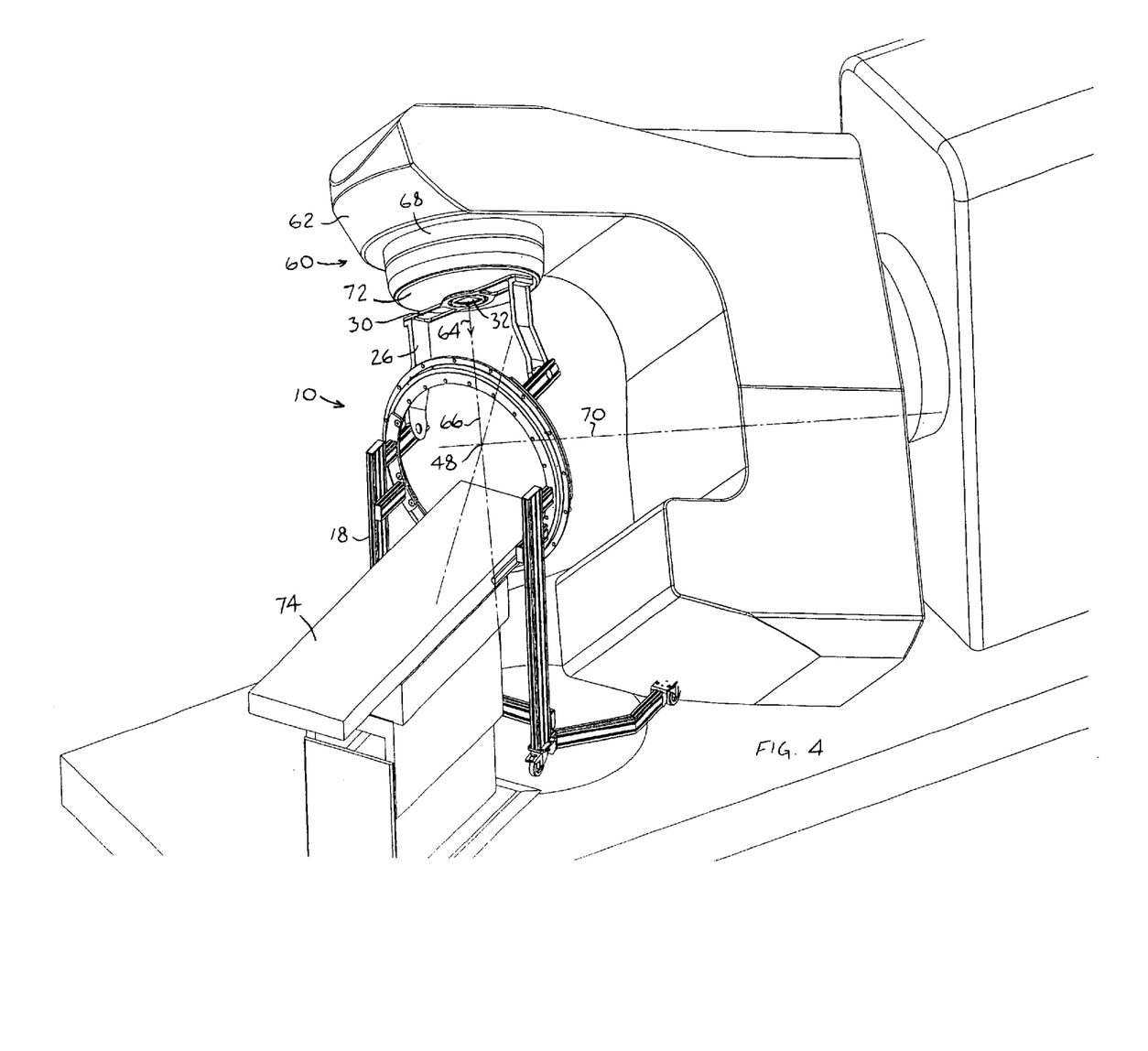
FIG. 4 is a simplified pictorial illustration of the imaging and treatment system of FIG. 3 with a patient support member (e.g., couch), in accordance with an embodiment of the present invention.

Reference is now made to FIGS. 3 and 4, which illustrate an imaging and treatment system 60, constructed and operative in accordance with an embodiment of the present invention. For the sake of simplicity, imaging apparatus 40 is omitted in FIGS. 3 and 4.

The imaging and treatment system 60 may include a treatment device 62 (e.g., a LINAC) operative to emit a treatment beam 64 (e.g., an electromagnetic wave or radiation beam) along a treatment axis 66 from a treatment source 68 (e.g., a radioactive source) mounted in treatment device 62. Treatment device 62 may be rotatable about a gantry axis 70. The treatment axis 66 and the gantry axis 70 may intersect at isocenter 48.

As mentioned above, the coupling arms 26 of coupler 10 may be rotatingly mounted on a turret 72 of treatment device 62 by means of interface member 30. The interface member 30 may be a bar or similar structure that connects coupling arms 26 together. The treatment beam 64 may pass through aperture 32. The coupling arms 26 are thus rotatable about the treatment axis 66. When imaging apparatus 40 is mounted on coupler 10 (as in FIG. 2), the coupling arms 26 maintain a spatial relationship between imaging apparatus 40 and treatment device 62 such that the imaging beam 44 (FIG. 2) and the treatment axis 66 intersect at an isocenter 48.

As seen in FIG. 4, the imaging and treatment system 60 may further include a patient support member 74 (e.g., a patient couch or table) rotatable about a turning axis, which in the non-limiting illustrated embodiment is the (azimuth) axis 52. Frame 18 may be secured to patient support member 74 so that coupler 10 (and imaging apparatus 40 mounted on coupler 10 as in FIG. 2) may be rotated about axis 52. The patient support member 74 may be moved to cause relative motion between the patient and the imaging and treatment isocenter 48. For example, the patient may be moved longitudinally along patient support member 74. Additionally or alternatively, patient support member 74 may be longitudinally movable along axis 14 to bring the patient in and out of the hollow bore 50. As the patient support member 74 is rotated about axis 52, coupler 10 may maintain the intersection of the imaging beam 44 (FIG. 2) and the turning axis 52 at isocenter 48. As mentioned above, the patient may be at least partially rotated about axis 52, and imaging apparatus 40 may still capture images of the patient as he/she is rotated about axis 52. Additionally, the coupler 10 may maintain a fixed angle between the imaging beam 44 and the treatment axis 66 during rotation of the imaging apparatus 40 (and of treatment device 62 about gantry axis 70), as is now explained with reference to FIGS. 5-7.

Figure 5:
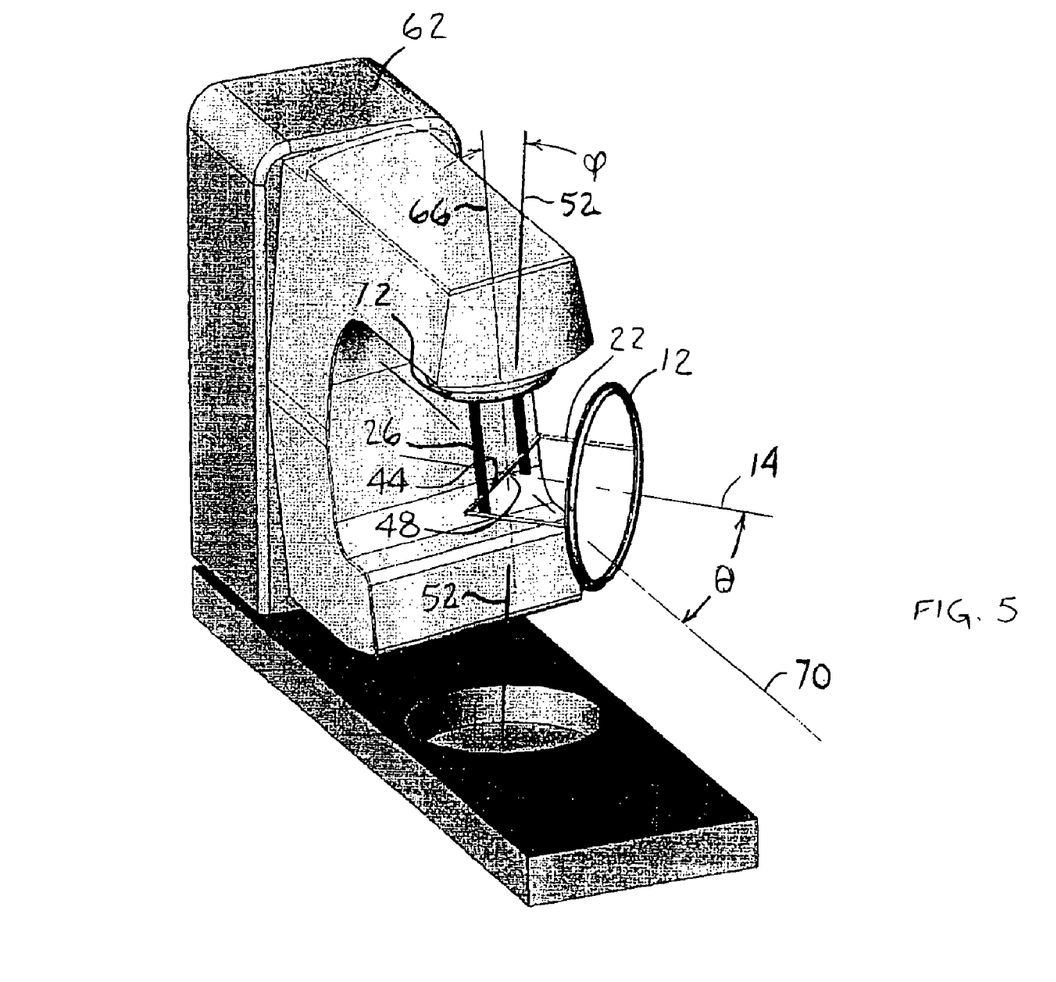
FIG. 5 is a simplified pictorial illustration of the imaging and treatment system of FIG. 3, with some elements omitted for the sake of simplicity, with the imaging apparatus arranged at an angle θ about a turning (azimuth) axis, and a gantry of the treatment device at an angle φ about a gantry axis, the imaging apparatus being attached to a rotatable member of the treatment device by the linkage arms, which can rotate about a treatment axis, wherein an imaging beam and the treatment axis intersect at an isocenter.

Reference is now made to FIG. 5, which illustrates rotator 12 of coupler 10 arranged at an angle $\theta$ about turning (azimuth or vertical) axis 38. The angle $\theta$ is measured between the central axis 14 of rotator 12 and gantry axis 70. The treatment device 62 is slightly rotated at an angle $\phi$ about gantry axis 70. The angle $\phi$ is measured between treatment axis 66 and turning axis 52. As mentioned above, the coupling arms 26 of coupler 10 that attach imaging apparatus 40 to turret 72 of treatment device 62 can rotate freely about treatment axis 66, and the imaging beam 44 and the treatment axis 66 intersect at isocenter 48.

Figure 6:
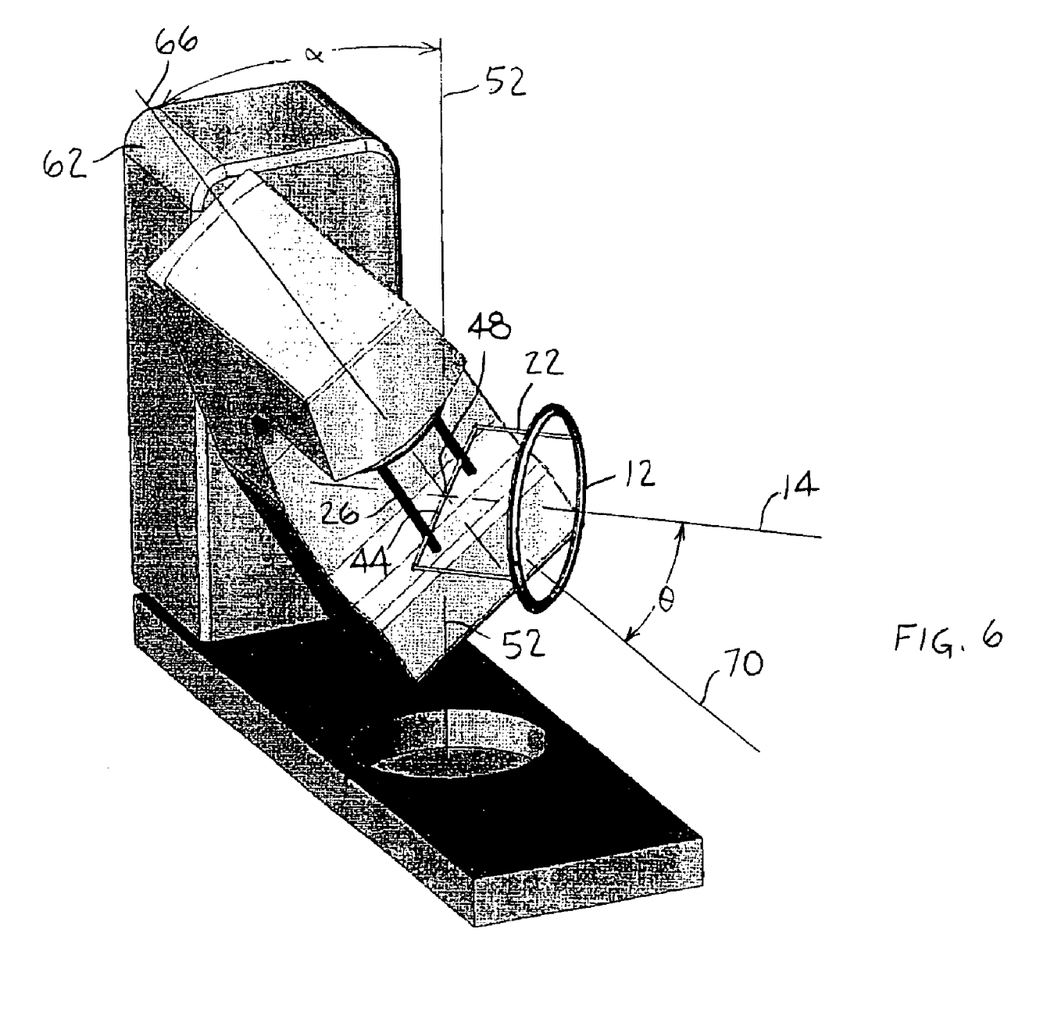
FIG. 6 is a simplified pictorial illustration of the imaging and treatment system of FIG. 1, with some elements omitted for the sake of simplicity, with the imaging apparatus maintained at angle θ about the turning axis and the imaging beam and the treatment axis still intersecting at the isocenter, even though the gantry has been rotated about the gantry axis through an angle α.

Reference is now made to FIG. 6. The rotator 12 of coupler 10 has been maintained at angle $\theta$ about the turning axis 52. The imaging beam 44 and the treatment axis 66 still intersect at isocenter 48, even though the gantry of treatment device 62 has been rotated about gantry axis 70 through a new angle $\alpha$. Thus, coupler 10 maintains the intersection of imaging beam 44 and turning axis 52 at isocenter 48. Additionally, coupler 10 maintains a fixed angle (in this case 90°) between the imaging beam 44 and the treatment axis 66 during rotation of the gantry of treatment device 62 about gantry axis 70.

Figure 7:
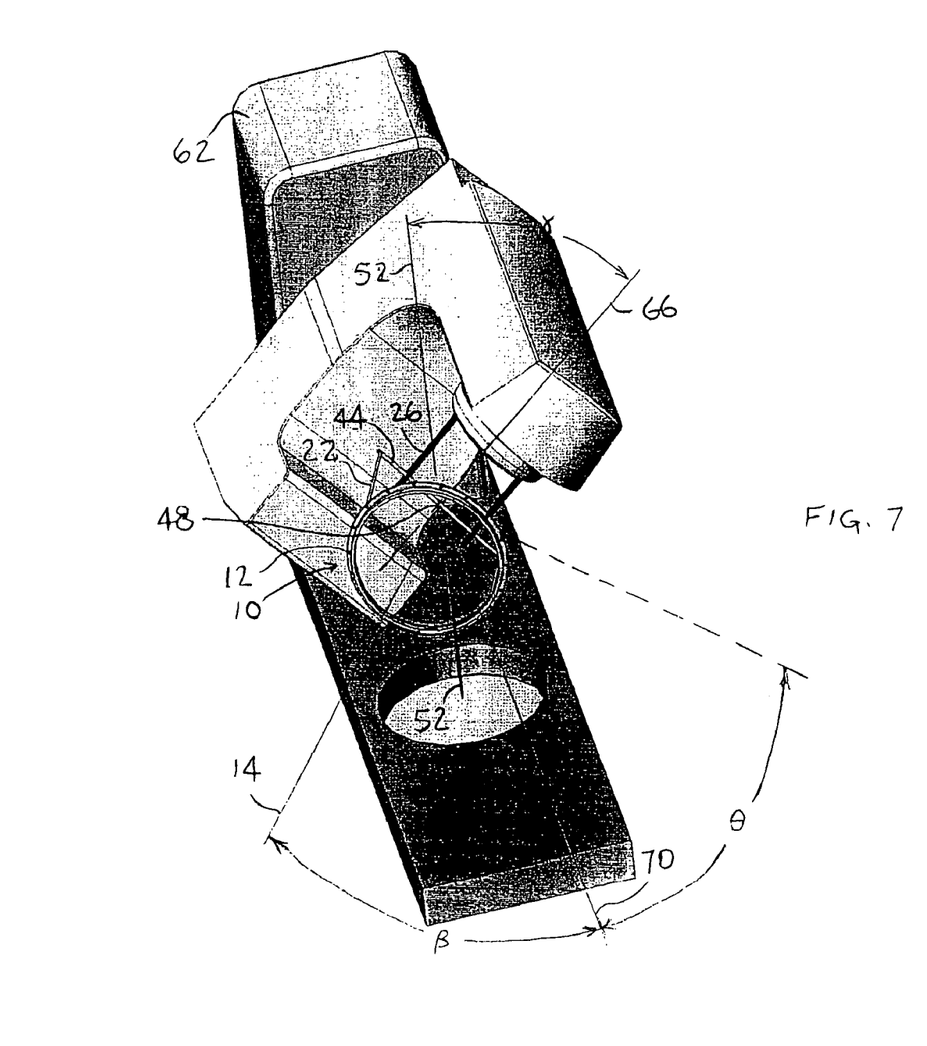
FIG. 7 is a simplified pictorial illustration of the imaging and treatment system of FIG. 1, with some elements omitted for the sake of simplicity, with the imaging apparatus rotated through a further angle β about the turning axis, and with the gantry rotated about the gantry axis through an angle γ, and the imaging beam and the treatment axis still intersecting at the isocenter.

Reference is now made to FIG. 7. The rotator 12 of coupler 10 has now been rotated through a further angle $\beta$ about turning axis 52. The gantry of treatment device 62 has been rotated about gantry axis 70 through an angle $\gamma$. Even with these rotations, the imaging beam 44 and the treatment axis 66 still intersect at isocenter 48. Thus again, coupler 10 maintains the intersection of imaging beam 44 and turning axis 52 at isocenter 48. Additionally, coupler 10 maintains a fixed angle (in this case 90°) between the imaging beam 44 and the treatment axis 66 during rotation of the imaging apparatus 40 about turning axis 52 and of the gantry of treatment device 62 about gantry axis 70.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An imaging device comprising:
    a rotator having a hollow bore for a patient to move therein and thereout, said rotator being rotatable about a longitudinal axis;
    at least one linkage arm extending outwards from said rotator;
    imaging apparatus mounted on said at least one linkage arm, the imaging apparatus comprising an imaging source that emits an imaging beam to an imaging detector aligned therewith along an imaging direction, said at least one linkage arm capable of full axial rotation about an imaging isocenter along an entire length of the patient, said isocenter lying along said longitudinal axis, and wherein the imaging apparatus is operative to rotate and to capture images of the patient along the imaging direction as the patient is positioned at an angle in a range of about 0-90° inclusive with respect to the longitudinal axis; and
    coupling arms pivotally attached to said linkage arms at pivots, said coupling arms being rotatingly attachable to a treatment device.

2. The imaging device according to claim 1, further comprising a patient support member movable to cause relative motion between the patient and said imaging isocenter.

3. The imaging device according to claim 1, wherein said rotator is rotatingly mounted to a stationary ring fixed to a portable frame.

4. The imaging device according to claim 1, wherein said coupling arms are rotatingly attachable to the treatment device by means of an interface member formed with an aperture for a treatment beam to pass therethrough.

5. The imaging device according to claim 1, wherein said coupling arms are rotatingly attached to a treatment device, said treatment device being rotatable about a treatment isocenter lying on a rotation axis and operable to emit a treatment beam along a treatment direction, wherein said treatment isocenter is located at an intersection of the rotation axis and the treatment direction.

6. The imaging device according to claim 5, wherein said treatment isocenter generally coincides with said imaging isocenter at a common isocenter.

7. The imaging device according to claim 6, further comprising a patient support member movable to cause relative motion between the patient and said imaging isocenter, wherein said patient support member is rotatable about an axis intersecting said common isocenter.

8. The imaging device according to claim 5, wherein said coupling arms are operable to maintain a fixed angle between the treatment direction and the imaging direction for a range of treatment device angles and imaging angles.

* * * * *